US012390561B2

(12) United States Patent
Masch et al.

(10) Patent No.: US 12,390,561 B2
(45) Date of Patent: Aug. 19, 2025

(54) OPHTHALMOLOGICAL COMPOSITION

(71) Applicant: Carl Zeiss Meditec AG, Jena (DE)

(72) Inventors: Jennifer-Magdalena Masch, Ratzeburg (DE); Michael Thaller, Berlin (DE)

(73) Assignee: Carl Zeiss Meditec AG, Jena (DE)

(*) Notice: Subject to any disclaimer, the term of this patent is extended or adjusted under 35 U.S.C. 154(b) by 511 days.

(21) Appl. No.: 17/891,837

(22) Filed: Aug. 19, 2022

(65) Prior Publication Data
US 2022/0401629 A1    Dec. 22, 2022

Related U.S. Application Data

(63) Continuation of application No. PCT/EP2021/053755, filed on Feb. 16, 2021.

(30) Foreign Application Priority Data

Feb. 20, 2020  (DE) ...................... 10 2020 104 540.9

(51) Int. Cl.
*A61L 31/04*    (2006.01)
(52) U.S. Cl.
CPC ................... *A61L 31/041* (2013.01)
(58) Field of Classification Search
None
See application file for complete search history.

(56) References Cited

U.S. PATENT DOCUMENTS

2011/0260125 A1* 10/2011 Zhang .................. C07D 311/92
                                                          252/586
2012/0085980 A2*  4/2012 Zhang .................. C08F 220/26
                                                          252/586
2016/0325009 A1* 11/2016 Cohn .................... A61L 24/0042
2018/0238745 A1*  8/2018 Nirkhe ..................... A61F 9/007
2018/0360743 A1* 12/2018 Bartynski ............... A61P 27/02
2019/0000871 A1*  1/2019 Jain ......................... A61P 27/02

(Continued)

FOREIGN PATENT DOCUMENTS

CN        102216353 A       10/2011
CN        111065359 A        4/2020
(Continued)

OTHER PUBLICATIONS

English translation and Office action of the Chinese Patent Office dated Feb. 14, 2023 for corresponding Chinese patent application 202180016134.0.
International Search Report of the European Patent Office dated Jun. 7, 2021 for international application PCT/EP2021/053755 on which this application is based.

(Continued)

*Primary Examiner* — Peter A Salamon
(74) *Attorney, Agent, or Firm* — Walter Ottesen, P.A.

(57) ABSTRACT

An ophthalmological composition includes at least one viscoelastic polymer, wherein the composition comprises at least one thermoresponsive compound that in a predefined wavelength range undergoes a temperature-dependent discontinuous change in at least one physical property from a group color and transmittance. The disclosure further relates to such an ophthalmological composition wherein a temperature-dependent change in the at least one physical property is reversible and/or wherein the temperature-dependent change in the at least one physical property occurs within not more than 10 seconds after a predefined temperature threshold value has been exceeded.

15 Claims, 4 Drawing Sheets

(56) References Cited

U.S. PATENT DOCUMENTS

| | | | |
|---|---|---|---|
| 2019/0209471 A1* | 7/2019 | Ladd | A61K 38/10 |
| 2019/0216335 A1* | 7/2019 | Stepien | A61B 5/411 |
| 2019/0233572 A1* | 8/2019 | Aitken | C08L 51/085 |
| 2019/0330523 A1* | 10/2019 | Li | C08L 23/06 |
| 2021/0179766 A1 | 6/2021 | Aitken et al. | |

FOREIGN PATENT DOCUMENTS

| | | |
|---|---|---|
| CN | 111712736 A | 9/2020 |
| EP | 3 089 766 A2 | 11/2016 |
| KR | 10-2004-0102473 A | 12/2004 |
| KR | 10-2016-0020297 A | 2/2016 |
| WO | 2013/020917 A1 | 2/2013 |
| WO | 2016/108071 A1 | 7/2016 |
| WO | 2018/156659 A1 | 8/2018 |

OTHER PUBLICATIONS

Translation of the Written Opinion of the International Searching Authority dated Jun. 7, 2021 for international application PCT/EP2021/053755 on which this application is based.

English translation and International Preliminary Report on Patentability dated Aug. 23, 2022 for international application PCT/EP2021/053755 on which this application is based.

Gutierrez, M. I. et al, "Therapy Ultrasound Equipment Characterization: Comparison of Three Techniques", 30th Annual International IEE EMBS Conference, Vancouver, Canada, Aug. 20-24, 2008, pp. 5117 to 5120.

Sorensen, T. et al, "Ultrasound-induced corneal incision contracture survey in the United States and Canada", J Cataract Refract Surg 2012; 38, copyright 2011 ASCRS and ESCRS, pp. 227 to 233.

* cited by examiner

OPHTHALMOLOGICAL COMPOSITION

CROSS REFERENCE TO RELATED APPLICATIONS

This application is a continuation application of international patent application PCT/EP2021/053755, filed Feb. 16, 2021, designating the United States and claiming priority from German application 10 2020 104 540.9, filed Feb. 20, 2020, and the entire content of both applications is incorporated herein by reference.

TECHNICAL FIELD

Disclosed are ophthalmological compositions.

BACKGROUND

In cataract surgery, clear and gel-like ophthalmological compositions (what are known as ophthalmic viscosurgical devices or ophthalmic viscoelastic devices, OVDs) are used during the ophthalmological procedure to create and maintain space in the anterior chamber of the eye and to protect the corneal endothelium. Conventional OVDs offer viscous and elastic properties, depending on the desired level of volume retention and coating protection. In phacoemulsification in particular, the use of OVDs offers significant benefits in order to reduce the risk of complications.

A large survey in the United States and Canada documented a 0.037% incidence of corneal wound burns for such eye surgeries (Sorensen T. et al. (2012): Ultrasound-induced corneal incision contracture survey in the United States and Canada. J Cataract Refract Surg, 38(2):227-233). Corneal wound burns (corneal burns) are a relatively rare but serious complication of phacoemulsification, the incidence of which, according to Sorensen, shows a significant inverse association with the surgeon's surgical volume. The ultrasonic movement of a phacoemulsification needle used for phacoemulsification can generate heat, which at a certain incision temperature of about 60° C. or higher can result in acute collagen damage at the incision site. Such burns are often associated with corneal oedema and severe surgically-induced astigmatism. Moreover, the corneal endothelium can be irreversibly destroyed by an increase in corneal temperature. Factors contributing to heat generation include the amount of phaco energy employed and a lack of adequate irrigation and aspiration. The phaco needle is therefore normally cooled by irrigation. However, any disturbance in the liquid flow or a liquid flow that is set too low can lead to an undesirable temperature rise. A further risk factor for corneal burns is the type of OVD used. When combined with ultrasound, certain OVDs can develop exothermic properties that result in an additional thermal energy input.

SUMMARY

Described are OVDs designed to reduce the risk of corneal wound burns during eye surgery.

The object can, for example, be achieved by an ophthalmological composition including at least one viscoelastic polymer, wherein said composition comprises at least one thermoresponsive compound that in a predefined wavelength range undergoes a temperature-dependent discontinuous change in at least one physical property from a group color and transmittance.

A first aspect relates to an ophthalmological composition comprising at least one viscoelastic polymer. The ophthalmological compositions described herein include at least one thermoresponsive compound that in a predefined wavelength range undergoes a temperature-dependent discontinuous change in at least one physical property from the group color and transmittance. In other words, described herein are thermoresponsive ophthalmological compositions that respond thermochromically when a defined temperature threshold is exceeded, that is, undergo a discontinuous change in its light absorption characteristics in the predefined wavelength range, and/or respond thermotropically, that is, undergo a change in transmission/translucency in the predefined wavelength range as a result of a phase transition. The ophthalmological compositions described herein also, in some embodiments, are referred to as an OVD (ophthalmological viscoelastic solution) and generally have varying viscosities. For example, the OVD described herein, in certain embodiments, is designed as a dispersive OVD or as a cohesive OVD or as a combined dispersive-cohesive OVD. Although surgeons already vary the surgical parameters in a phacoemulsification, there is currently no feedback on the effectiveness of these parameters as regards intraocular temperature or temperature distribution. With the aid of the OVDs described herein, the risk of a corneal wound burn during eye surgery is significantly reduced, since the OVD gives the surgeon feedback on the intraocular temperature and, in particular, an immediate warning when a predefined temperature threshold value is exceeded. Besides the conventional features of OVDs that are already known, the additional thermoresponsive property of the OVDs described herein provides a temperature indicator that enables the surgeon to immediately change the surgical technique if necessary in order to avoid heat damage. This gives the surgeon better control over how the currently applied phaco energy and also the current rates of irrigation and aspiration are affecting the intraocular temperature. This feedback on the intraocular temperature during phacoemulsification in cataract surgery makes surgical treatment much safer, it being of course possible in principle to use the ophthalmological compositions described herein not just in the treatment of cataracts, but in other types of surgery too. A major benefit is envisaged for the addition of the thermoresponsive compound(s) to dispersive OVDs, which are typically used during surgery to protect the corneal endothelium, which does not regenerate. Intraoperative surgical trauma can cause irreversible endothelial failure. Since wound healing or regeneration of the corneal endothelium do not occur, dispersive OVDs having thermoresponsive properties offer both coating protection of the corneal endothelium and also a temperature sensor on the corneal endothelium. They thus provide important information about temperature changes in this sensitive cell layer. The thermoresponsive compound(s) within the OVD are in some instances designed such that above a temperature threshold they undergo a change in their appearance either from colorless to colored (thermochromism) and/or from transparent to non-transparent (thermotropism). In addition to a change from colorless to colored or from transparent to non-transparent, in some embodiments, there are also multiple changes in color and/or transparency, each with different temperature threshold values. The degree of coloration/transparency of the thermoresponsive OVD offers the surgeon the opportunity, in the event of an increase in intraocular temperature, of indicating the intraocular temperature with low to high coloration and/or high to low transparency. The thermoresponsive compound is in some embodiments non-toxic or toxicologically tolerable and/or biodegradable.

In an advantageous embodiment, a temperature-dependent change in the at least one physical property is reversible or irreversible. In the case of reversible changeability of the thermoresponsive compound, in some embodiments the ophthalmological compositions indicate not only that a threshold temperature has been exceeded, but also that the temperature has subsequently fallen below this value, for example when a surgeon has made an appropriate correction to the surgical parameters. In embodiments of irreversible changeability of the thermoresponsive compound, the ophthalmological compositions described herein signal a termination of the operation, for example when an impermissibly high temperature value has been reached. Alternatively or in addition, the temperature-dependent change in the at least one physical property occurs within not more than 10 seconds, or within not more than 2 seconds, after a predefined temperature threshold value has been exceeded. In other words, the thermoresponsive compounds undergo a discontinuous change in its optical properties with the maximum possible rapidity after the temperature threshold value has been exceeded, namely within 10 s, 9 s, 8 s, 7 s, 6 s, 5 s, 4 s, 3 s, 2 s, 1 s, or less. This allows feedback about an impermissible rise in temperature to be as prompt as possible, which means that a correspondingly swift correction to the surgical parameters can be made before damage to the eye tissue occurs.

Further advantages arise when the at least one thermoresponsive compound is selected from a group comprising polymers, interpenetrating polymer networks, semi-interpenetrating polymer networks, liquid crystals, in particular cholesteric liquid crystals, pigments, dyes, inks, microcapsules, and any combinations thereof. This makes it possible to optimally adjust not just the thermoresponsive properties, but also additional properties of the ophthalmological composition such as rheology, miscibility of the individual components, et cetera. By using microcapsules, it is possible to use also short-chain thermoresponsive compounds and thermoresponsive compounds that are poorly soluble or poorly miscible with the viscoelastic polymer. Microencapsulation in some embodiments employs a colorless or transparent compound in which the thermoresponsive compound(s) is/are enclosed. In some embodiments, a gelatin, a substituted or unsubstituted (meth)acrylate, a glycosaminoglycan and the like are used as the shell of the microcapsule. In a further embodiment, the microcapsules are covalently attached to the viscoelastic polymer, which ensures particularly reliable protection against outward diffusion of the thermoresponsive compound(s).

In a further advantageous embodiment, the at least one thermoresponsive compound comprises at least one constitutional unit selected from poly(N-isopropylacrylamide), poly(N,N-diethylacrylamide), poly(methyl vinyl ether), poly(N-vinylcaprolactam), a block copolymer of poly(ethylene oxide) and poly(propylene oxide), a poly(pentapeptide) of elastin, an interpenetrating network of polyacrylamide and polyacrylic acid, and copolymers thereof. In the context of the present disclosure, a copolymer is understood as meaning not only copolymers having two monomer types or two repeat units, but also polymers having three monomer types or repeat units (triblock copolymers) or four or more monomer types or repeat units. In addition, the term copolymer in the context of the present disclosure encompasses all possible sequences of the constitutional repeat units, thus for example random copolymers, alternating copolymers, block copolymers, graft copolymers, gradient copolymers, et cetera. Likewise, all possible tacticities, that is, atactic, isotactic, and syndiotactic arrangements of individual repeat units in the macromolecule, are considered to be included in the disclosure. In addition, polymer blends of different homopolymers and/or copolymers are possible. Through the selection of the constitutional units or repeat units and by varying their composition and the way in which they are linked, it is possible to optimally adapt to the use in the particular case not just the threshold temperature value for the phase change, but also the color and transmission properties above and below the threshold temperature value or phase transition.

In a further advantageous embodiment, the at least one viscoelastic polymer comprises a polysaccharide selected from glycosaminoglycans, cellulose, a cellulose ether with methyl and/or ethyl and/or propyl groups, in particular hydroxypropylmethylcellulose, hydroxyethylmethylcellulose and/or methylcellulose, a glycosaminoglycan, in particular hyaluronic acid, chondroitin sulfate, dermatan sulfate, heparin, heparan sulfate, keratan sulfate, alginic acid, polymannuronic acid, polyguluronic acid, polyglucuronic acid, amylose, amylopectin, callose, chitosan, polygalactomannan, dextran, xanthan and/or any mixture thereof, copolymers thereof, and pharmacologically acceptable salts thereof. This allows the viscoelastic properties of the OVD to be optimally adapted to the intended use in the particular case. The OVDs also in some embodiments comprise two or more polysaccharides of the same type that differ only in respect of one or more parameters.

In a further advantageous embodiment, the at least one thermoresponsive compound is covalently linked to the at least one viscoelastic polymer, such as via a spacer. This advantageously prevents the thermoresponsive compound from diffusing out of the ophthalmological composition. Optionally, a spacer or crosslinker is included for easy covalent attachment and/or to avoid any steric hindrance in the thermoresponsive compound and/or in the viscoelastic polymer. Alternatively or in addition, the at least one thermoresponsive compound is present in the form of particles and/or microspheres dispersed in the at least one viscoelastic polymer.

Such thermoresponsive particles, for example microparticles and/or nanoparticles or microspheres, can be achieved for example by incorporating thermochromic dyes. These thermochromic dyes can reversibly form stable delocalized electron systems capable of absorbing light in the visible spectrum when the temperature increases, for example through reversible ring-closure reactions. Alternatively or in addition, the at least one viscoelastic polymer and the at least one thermoresponsive compound form a semi-interpenetrating and/or interpenetrating network. Interpenetrating polymer networks (IPNs) have the characteristic feature of comprising two or more networks that are at least partially entangled at the molecular level but are not covalently bound to one other. They therefore cannot be separated unless chemical bonds are broken. This also reliably prevents the thermoresponsive compound from diffusing out. Semi-interpenetrating polymer networks (SIPNs) have the characteristic feature of comprising one or more networks and one or more linear or branched polymer(s) that interpenetrate at the molecular level. This means that the linear or branched polymers can in principle be separated from the constituting polymer network(s) without having to break chemical bonds. Here too, there is however normally reliable protection against undesired outward diffusion.

In a further advantageous embodiment, the at least one thermoresponsive compound exhibits thermochromic and/or thermotropic behavior when a predefined temperature value within a temperature range of between 10° C. and 80° C. is exceeded. In other words, in the event of an increase in temperature, the at least one thermoresponsive compound independently undergoes a dramatic change in its color and/or transmittance as soon as the predefined temperature value, for example 10° C., 11° C., 12° C., 13° C., 14° C., 15° C., 16° C., 17° C., 18° C., 19° C., 20° C., 21° C. 22° C., 23° C., 24° C., 25° C., 26° C., 27° C., 28° C., 29° C., 30° C., 31° C. 32° C., 33° C., 34° C., 35° C., 36° C., 37° C., 38° C., 39° C., 40° C., 41° C. 42° C., 43° C., 44° C., 45° C., 46° C., 47° C., 48° C., 49° C., 50° C., 51° C. 52° C., 53° C., 54° C., 55° C., 56° C., 57° C., 58° C., 59° C., 60° C., 61° C. 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C., is exceeded. Through this, it is possible to achieve optimal adjustment of the desired temperature change to the discontinuous change in the optical property. The at least one thermoresponsive compound is in some embodiments selected such that the temperature value predefined for the change in appearance is not higher than about 60° C., since corneal burns must be expected above this temperature. The predefined temperature value is in some embodiments not higher than 40° C. and is in some embodiments within the temperature range above the intraocular temperature, that is, between about 35° C. and about 38° C. In the case of thermoresponsive compounds that can undergo a reversible change in their optical properties, the thermoresponsive compound would accordingly readopt its original optical properties or the properties that it has at room temperature once the temperature has fallen below a threshold value. The predefined temperature value when heating and the temperature threshold value when cooling down may in some cases be identical. As a consequence of hysteresis effects, different threshold values may in some cases also arise when heating and cooling down again. Alternatively or in addition, the at least one thermoresponsive compound has, in a first temperature range below 60° C., or below 45° C., and in some embodiments above 38° C., a first color and/or transmission property and, in a second temperature range that is above the first temperature range, a second color and/or transmission property that is different from the first color and/or transmission property. In some embodiments, the at least one thermoresponsive compound does not in either state have a visible light emission or a strongly light-scattering state, since this would produce a permanently colored or permanently non-transparent or at least not clearly translucent OVD that could impair the surgeon's vision during cataract surgery.

In a further advantageous embodiment, the at least one thermoresponsive compound is in the first temperature range at least essentially colorless and/or at least mostly transparent and/or the at least one thermoresponsive compound is in the second temperature range colored and/or at least mostly part non-transparent. In other words, in the first temperature range, which is accordingly considered tolerable and risk-free or at least low-risk, the at least one thermoresponsive compound as far as possible does not cause any optical interference due to chromaticity, at least in the wavelength range visible to humans, and/or due to reduced transmission. This means that a surgeon is not adversely affected during eye surgery, provided the temperature is within an acceptable range and provided the temperature threshold between the first and second temperature ranges is not exceeded. However, as soon as this temperature threshold is exceeded, this results in an immediate optical warning through the at least one thermoresponsive compound assuming a color or changing its color and/or becoming at least mostly non-transparent, thereby giving the treating physician a clear warning signal that temperature-lowering measures are required.

In a further advantageous embodiment, the predefined wavelength range is between 50 μm and 200 nm, or between 780 nm and 315 nm. In other words, in accordance with the invention the at least one thermoresponsive compound undergoes a temperature-dependent discontinuous change in color and/or transmittance in the UV-B, UV-A, human-visible light, near-infrared (IR A, IR B) or mid-infrared ranges (IR C). A change in the visible range (approx. 380 nm to 780 nm) has the advantage that it can be detected by the treating physician immediately and without additional aids. A change in the IR or UV range can on the other hand be detected using a suitable detection apparatus and has the advantage that the change in the optical property has no effect in the visible range, allowing a surgeon to continue with the operation undisturbed.

The predefined wavelength range is, for instance, 780 nm, 775 nm, 770 nm, 765 nm, 760 nm, 755 nm, 750 nm, 745 nm, 740 nm, 735 nm, 730 nm, 725 nm, 720 nm, 715 nm, 710 nm, 705 nm, 700 nm, 695 nm, 690 nm, 685 nm, 680 nm, 675 nm, 670 nm, 665 nm, 660 nm, 655 nm, 650 nm, 645 nm, 640 nm, 635 nm, 630 nm, 625 nm, 620 nm, 615 nm, 610 nm, 605 nm, 600 nm, 595 nm, 590 nm, 585 nm, 580 nm, 575 nm, 570 nm, 565 nm, 560 nm, 555 nm, 550 nm, 545 nm, 540 nm, 535 nm, 530 nm, 525 nm, 520 nm, 515 nm, 510 nm, 505 nm, 500 nm, 495 nm, 490 nm, 485 nm, 480 nm, 475 nm, 470 nm, 465 nm, 460 nm, 455 nm, 450 nm, 445 nm, 440 nm, 435 nm, 430 nm, 425 nm, 420 nm, 415 nm, 410 nm, 405 nm, 400 nm, 395 nm, 390 nm, 385 nm, 380 nm, 375 nm, 370 nm, 365 nm, 360 nm, 355 nm, 350 nm, 345 nm, 340 nm, 335 nm, 330 nm, 325 nm, 320 nm, or 315 nm, all intermediate values and ranges being considered to be disclosed too.

Also disclosed is a detection apparatus for cataract surgery. The detection apparatus comprises at least one optical sensor system, by means of which a discontinuous change in a physical property from the group color and transmittance of an ophthalmological composition (OVD) can be detected in accordance with the first aspect, and at least one human-machine interface coupled to the sensor system for data exchange, by means of which a visual and/or acoustic and/or haptic indication to a user can be generated in the event of detection of a discontinuous change in the color and/or transparency of the OVD. This makes it possible to significantly reduce the risk of a corneal wound burn during eye surgery, since a change in color and/or transparency detected by the detection apparatus can be immediately signaled to the surgeon by means of the human-machine interface. The surgeon can then take immediate countermeasures to bring the temperature down to an acceptable level. In some embodiments of the OVD, the sensor system is adapted to different wavelengths or wavelength ranges in order to monitor the thermochromic or thermotropic behavior of the thermoresponsive compound. For example, the sensor system is in such embodiments configured for monitoring in the UV-B and/or UV-A range, in the range of light visible to humans, in the near infrared (IR A, IR B) and/or in the middle infrared (IR C). Any combinations thereof are also contemplated herein. The detection apparatus is, in some embodiments, configured as a standalone independent device. In some embodiments, all elements of the detection apparatus here are arranged in a common housing. Alternatively, in some embodiments, certain elements of the detection apparatus are spaced apart from one another. For example, in such embodiments, data exchanges between the sensor system and the human-machine interface take place in a cabled and/or wireless manner. Alternatively, in other embodiments, the detection apparatus is partly or completely integrated into another device or else makes use of existing devices. For example, in such an embodiment, a camera that is already present in an OP microscope is used as the sensor system for acquiring image data. Likewise, an existing computing device is used to analyze and check the image data of the sensor system and/or to control or regulate the human-machine interface according to the test result of the image data.

BRIEF DESCRIPTION OF THE DRAWINGS

The invention will now be described with reference to the drawings wherein.

DESCRIPTION OF THE PREFERRED EMBODIMENTS

Figure 1:
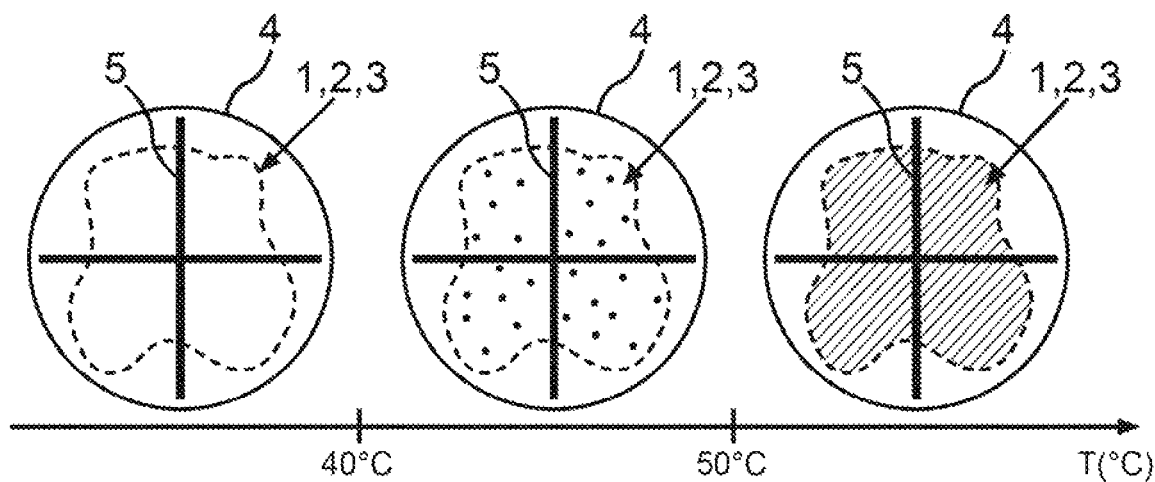
FIG. 1 shows schematic views of an ophthalmological composition (OVD) as described herein at various temperatures, the OVD comprising a viscoelastic polymer and a thermoresponsive compound that undergoes a temperature-dependent discontinuous change in color in the visible wavelength range.

FIG. 1 shows three schematic views of an ophthalmological composition (OVD) 1 at about 35° C., about 45° C., and about 55° C. in the temperature range between about 30° C. and 60° C. The OVD 1 comprises a viscoelastic polymer 2 in which a thermoresponsive compound 3 is uniformly dispersed. In the present working example, the thermoresponsive compound 3 has thermochromic properties and undergoes a temperature-dependent discontinuous change in color in the wavelength range visible to humans. For clarity, the OVD 1 is shown in a sample vessel 4 symbolizing a surgical field, which has a Cartesian coordinate system 5. It can be seen that the OVD 1 is colorless and highly transparent below 40° C., for example at 35° C., becomes slightly colored at about 45° C., and at about 55° C. has undergone a discontinuous color change that can be detected with the naked eye or with a corresponding sensor system 6 (see FIG. 9).

Figure 2:
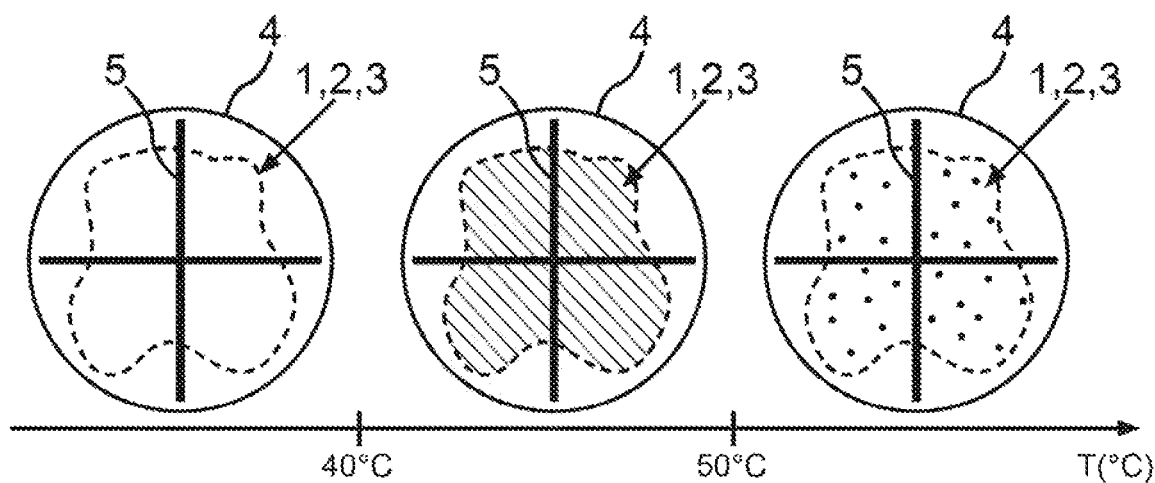
FIG. 2 shows schematic views of the OVD described herein at various temperatures, the OVD comprising a viscoelastic polymer and a thermoresponsive compound that undergoes a temperature-dependent discontinuous change in color in the infrared wavelength range.

FIG. 2 shows schematic views of the OVD 1 at about 35° C., about 45° C., and about 55° C. in the temperature range between about 30° C. and 60° C. In contrast to the previous working example, the thermoresponsive compound 3 undergoes a temperature-dependent discontinuous change in color in the near-infrared wavelength range. Below 40° C., the OVD 1 is again colorless and highly transparent and becomes colored in a discontinuous manner above about 40° C., the OVD 1 emitting longer wavelengths than visible light as the temperature increases. This color change is therefore usually not detectable by eye, but can be detected with a corresponding sensor system 6.

The one or more thermoresponsive compounds 3 within the OVD 1 are in some embodiments designed such that they undergo a change in their appearance either from colorless to colored (thermochromism) and/or from transparent to non-transparent (thermotropism) when a defined temperature threshold is exceeded. In addition to a change from colorless to colored or from transparent to non-transparent, there may also be multiple temperature-dependent changes in color and/or transparency. The degree of coloration/transparency of the thermoresponsive OVD 1 offers the surgeon the possibility of indicating the intraocular temperature or—when a temperature threshold has been exceeded due to an increase in the intraocular temperature—of showing a rapid transition between weak and strong coloration and/or between high and low transparency. The temperature defined for the change in appearance is optimized to a certain threshold value, for example 40° C. Temperature values that are safe for the human cornea are generally in a range from about 32° C. to about 38° C. The critical temperature for a corneal burn is generally considered to be 60° C.

One way of producing a thermoresponsive OVD 1 is by modifying a viscoelastic polymer with thermoresponsive particles. This can be achieved for example by integrating dyes in the form of a thermochromic compound 3 into a polymer network. These dyes 3 are able to reversibly form stable delocalized electron systems capable of absorbing light in the visible spectrum when the temperature increases, for example through reversible ring-closure reactions. Preferably, a dye 3 is used here that emits in the far or near infrared spectrum while the temperature is below a critical temperature threshold, and emits in the human visible spectrum (or in the near infrared spectrum) when the temperature is above the predefined temperature threshold (cf. FIG. 1, FIG. 2). In some embodiments, the dye 3 does not have a visible light emission in either state, since this would create a permanently colored OVD 1 that could impair a surgeon's vision during cataract surgery.

As an alternative or in addition to a thermochromic compound 3, it is also possible to use thermotropic compounds 3 that develop turbidity when a predefined temperature threshold is exceeded. This can be investigated experimentally, for example by turbidimetry, the temperature at a defined transmission of 50% being considered the temperature threshold in the context of the present disclosure.

Figure 3:
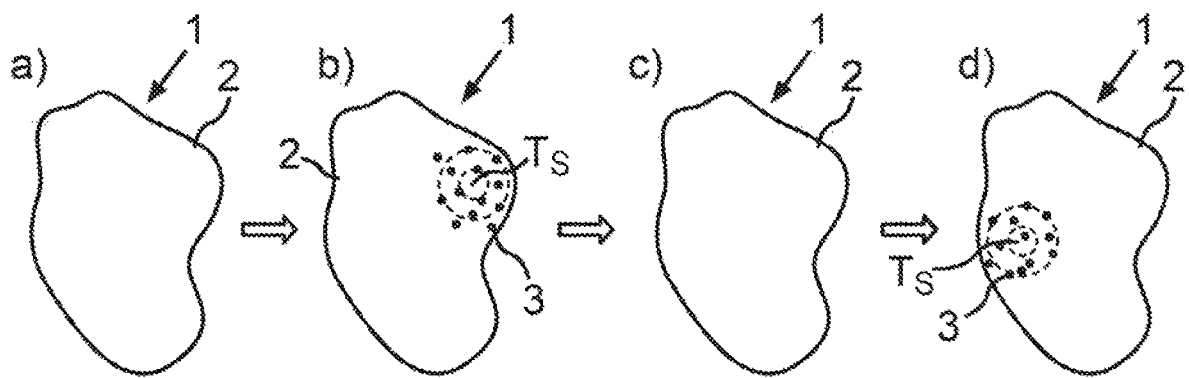
FIG. 3 shows schematic views of the OVD described herein at various local temperatures, the OVD comprising a viscoelastic polymer and a thermoresponsive compound that are present in the viscoelastic polymer in the form of microbeads.

FIG. 3 shows four schematic views of the OVD 1 at various local temperatures. The thermoresponsive compound 3 is present dispersed in the form of microbeads in the viscoelastic polymer 2. The microbeads 3 can be attached to the polymer 2 covalently. Below their phase transition temperature, the microbeads 3 are invisible (a). When a heat source heats the temperature locally above the phase transition temperature/threshold temperature $T_T$, these microbeads 3 undergo a phase transition and become visible (b). Once the temperature has fallen back below the phase transition temperature $T_T$, the microbeads 3 become invisible again (c). If the temperature at another location locally rises above the phase transition temperature $T_T$, the microbeads 3 become visible again at the location concerned (d).

In addition to or instead of short-chain compounds or compounds present in the form of microbeads 3, thermoresponsive polymers that reversibly switch their optical properties when a defined temperature threshold is reached are also possible. Examples of suitable polymers include repeat units of poly(N-isopropylacrylamide) (PNIPAM) or a variety of similar copolymers such as poly(ethylene glycol) (PEG) and/or poly(ε-caprolactone) (PCL). During their phase transition, such polymers undergo a change between fully transparent and mostly or fully opaque. This means that they are invisible to the eye below their phase transition temperature $T_T$ and become visible above the phase transition temperature $T_T$. Furthermore, it is also possible to use these polymers to produce microparticles or other small-scale structures that can undergo the swiftest-possible phase transitions. In addition, it is possible to incorporate into these polymers reactive groups that could be used for chemical linking with viscoelastic polymer chains within the OVD 1. As a result, the resulting OVD 1 possesses, so to speak, localized thermoresponsive sensors capable of detecting a local temperature rise above a certain threshold value.

This offers the advantage that these microspheres are completely invisible to the naked eye, provided the temperature is below the phase transition temperature for these polymers. This means that the surgeon is able to perform the operation without visual hindrances caused by the "sensors" 3, provided the intraocular temperature is below the critical threshold. As soon as the temperature rises, the phase transition of the thermoresponsive particles 3 would become visible to the human eye in the heated area and warn the physician of a temperature rise. In some embodiments, the phase transition of the thermoresponsive particles 3 is registered via an imaging sensor integrated into the surgical microscope. A sophisticated imaging camera has the advantage of greater sensitivity compared to the surgeon's eye. Through the eyepiece of a surgical microscope and/or on a digital screen as a human-machine interface, a real-time overlay of the surgical image and of the optionally amplified color signal detected from the thermoresponsive OVD 1 provides information about the temperature distribution within the surgical field. This option also enables the detection of a weak OVD color/transparency signal and shortens the surgeon's response time. In principle it is possible to provide an interface between the surgical microscope and the phaco machine that allows any necessary control and/or regulation of the phaco machine parameters to be carried out for automatic adjustment of the currently supplied phaco energy and/or of the rate of irrigation and/or aspiration.

Described hereinbelow are various production options for thermoresponsive OVDs 1 based on thermoresponsive polymers 2. The thermoresponsive compounds 3 used are in some instances non-toxic or toxicologically tolerable, offer a mechanism for attachment to viscoelastic polymers 2, and exhibit a discontinuous color and/or transparency transition at a defined temperature threshold or within the narrowest possible temperature range (for example within 5-10 K).

Various thermoresponsive polymers 2 are known per se and have previously been prepared in various variants, for example poly(N-isopropylacrylamide) (PNIPAM), poly[2-(dimethylamino)ethyl methacrylate], hydroxypropyl cellulose, or polyvinyl methyl ether. The most popular group of these polymers is based on PNIPAM having the general formula I:

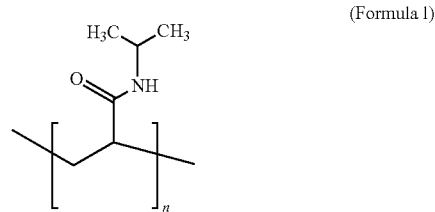

(Formula I)

Since the production of PNIPAM is based on acrylate polymerization, there are many options for producing copolymers based on this acrylamide having a variety of different phase transition temperatures. The basic mechanism for the phase transition in thermoresponsive polymers is the same in all cases, namely a temperature-dependent dramatic shift in the thermodynamic interactions between polymer and water. Below the phase transition temperature, it is thermodynamically more favorable for the polymer chain to interact with the surrounding water molecules. In this state, the polymer chains exist as an elongated chain and are invisible to the eye. Above the phase transition temperature, it becomes more favorable for the polymer chains to interact with themselves and to exclude water from their network. In this state they exist as collapsed polymer chains and are able to scatter light. This interaction means that an aqueous solution of PNIPAM or similar polymers is transparent below the phase transition temperature and becomes opaque above this temperature.

The phase transition temperature can be modulated by introducing other monomer types, such as acrylates and/or acrylamides, so as to create tailored copolymers. This allows the creation of thermoresponsive compounds 3 capable of "detecting" various temperature thresholds. Furthermore, these compounds 3 are in some embodiments introduced into various structures such as macroscopic gels or microparticles. Encapsulation can also be envisaged for certain embodiments. Furthermore, copolymerization allows the introduction of other reactive groups that can be used for covalent attachment of such thermoresponsive compounds 3 to other carrier molecules, for example hyaluronic acid or other viscoelastic polymers.

Presented hereinbelow are two possibilities as examples of how thermoresponsive OVDs 1 can be realized. A first possibility shown in FIG. 4 includes the covalent attachment of thermoresponsive polymer strands TRP to viscoelastic polymers OVDP. A second possibility shown in FIG. 5 includes the covalent attachment of thermoresponsive microspheres TRP with viscoelastic polymers OVDP. It should at this point be stressed that the embodiments described herein are not limited to these examples, since there is a large variety of possible polymers/copolymers and production options for realizing an OVD 1.

As previously described, one possible strategy for producing a thermoresponsive OVD 1 is to modify the viscoelastic polymers 2 with thermoresponsive compounds 3. This can be realized with the following general approach:
1) Modification of the viscoelastic polymers (OVDP) 2 of the OVD 1 with reactive groups (FIG. 4, FIG. 5: 1*b*).

Figure 4:
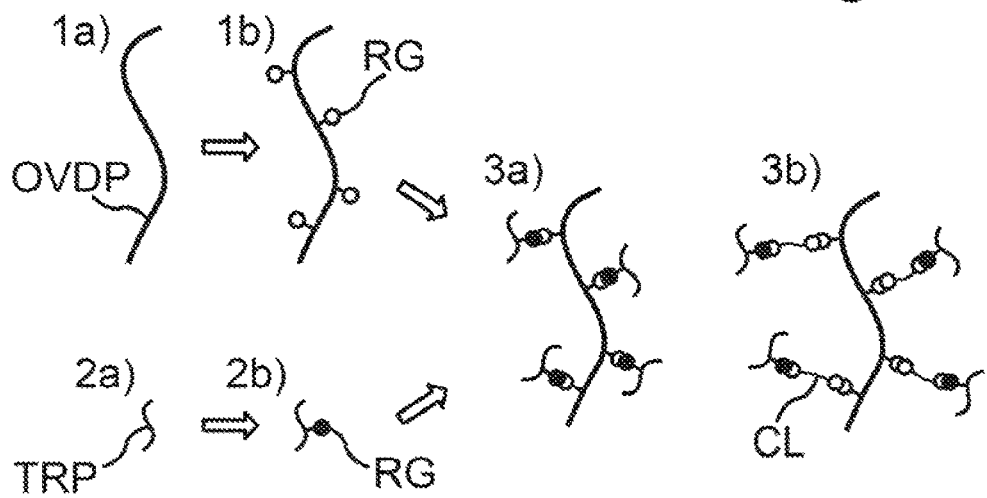
FIG. 4 shows a first approach to the production of a thermoresponsive OVD by crosslinking a thermoresponsive compound with a viscoelastic polymer.
Figure 5:
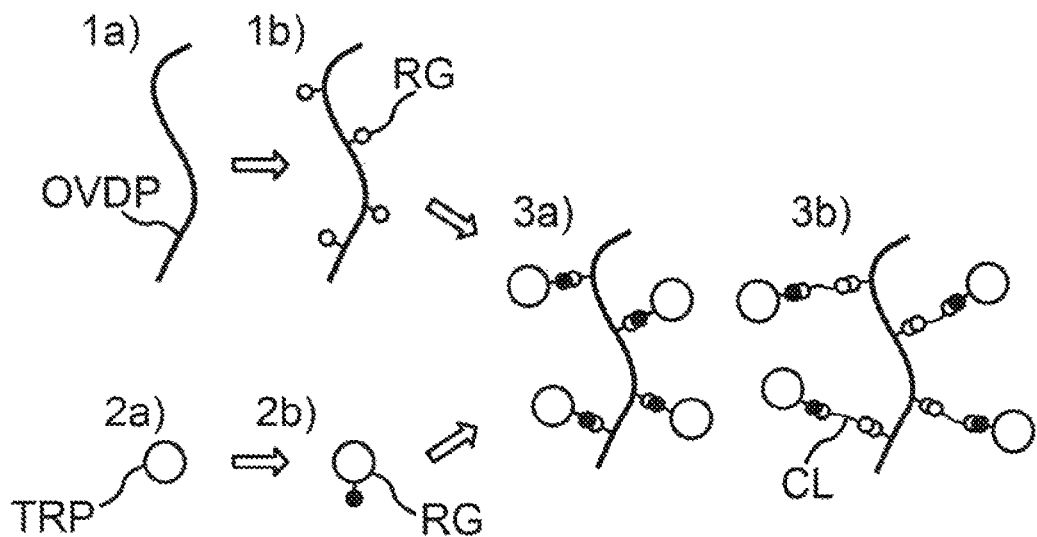
FIG. 5 shows a second approach to the production of a thermoresponsive OVD by crosslinking microbeads of a thermoresponsive compound with a viscoelastic polymer.

2) Modification of the "thermoresponsive polymers" (TRP) 3 with reactive groups RG (FIG. 4, FIG. 5: 2*b*) that, in the case of complementary RGs, allow direct linking of the TRP 3 to the OVDP 2 (FIG. 4, FIG. 5: 3*a*).
3) Covalently linking the reactive groups RG of the OVDPs 2 to reactive groups RG of the TRPs 3 via a corresponding crosslinker CL (FIG. 4, FIG. 5: 3*b*). The reactive groups RG can generally be selected independently of one another and can be identical or different. Depending on the subsequent intended use of the OVD 1, the TRPs 3 can be attached as individual polymer chains (FIG. 4) or in the form of polymer microparticles (FIG. 5).

In the first approach, individual strands of the TRPs 3 are covalently linked to the OVDPs 2. This is achieved in certain embodiments by modifying both reactants with chemically reactive groups RG. If these RG groups are mutually complementary, they will react directly with one other and permit direct attachment of the TRPs 3 to the OVDPs 2 (FIG. 4, FIG. 5: 3*a*). On reaching their threshold temperature, the TRPs 3 will then undergo a phase transition, producing local turbidity and/or coloration. This is the simplest way of producing a thermoresponsive OVD 1. However, the short distance between the two reactants can give rise to steric/physical interactions that adversely affect the ability of the TRPs 3 to undergo the temperature-dependent phase transition. Therefore, in an alternative configuration, crosslinkers CL are used to anchor the TRPs 3 at a greater distance from the OVDPs 2. The TRP chains 3 are then able to behave more independently of the OVDPs 2, depending on the chosen length of the crosslinkers CL.

As already mentioned, an alternative is to use TRP microparticles instead of individual TRP strands. These entities can undergo very rapid phase transitions, which is advantageous in order to permit swift detection of whether a predefined temperature threshold has been exceeded during eye surgery. Depending on the size and distribution of these particles, the visual reaction when a temperature threshold has been reached is not a general opacification or coloration in the heated area, but the appearance of small "dots" as shown in FIG. 3. In some cases, this provides physicians with more desirable visual feedback that has less disruptive impact on the surgery. However, this makes the production process somewhat more complex, since the microparticles first have to be synthesized from individual strands of TRP.

Compounds from the group of polysaccharides are commonly used as viscoelastic polymers 2 for OVDs 1. Hyaluronic acid (HA, formula II a)) has been found to be particularly suitable. A major advantage of this group of macromolecules is their ability, through the presence of carboxyl functionalities, to be easily modified with further chemical groups by means of well-explored and established EDC (1-ethyl-3-[3-dimethylaminopropyl]carbodiimide)/NHS (N-hydroxysuccinimide) peptide-coupling chemistry. This is shown schematically in formula II b):

(Formula II)

a)
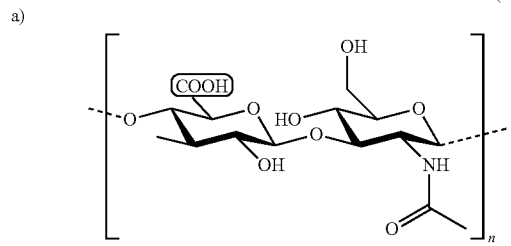

b)
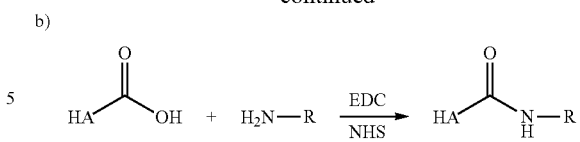

The reactive carboxyl group of the HA for further chemical modifications is circled in formula II a). Formula II b) shows the reaction scheme for the EDC/NHS-mediated peptide coupling reaction. "HA" here represents the hyaluronic acid backbone. "R" is either the reactive group that is attached to HA, a spacer that leads directly to the TRP, or a crosslinker that is subsequently attached to the optionally correspondingly modified TRP.

This type of reaction can be used to introduce a reactive group to which an amide-modified TRP can bond. Likewise, this type of reaction can be used to attach another reactive group to HA for subsequent attachment to the TRP or crosslinking to a third group.

Polysaccharides and especially HA are therefore favorable candidates for this embodiment. However, other viscoelastic polymers can also be modified in other ways, chemically coupled with thermoresponsive compounds 2, and used to produce a thermoresponsive OVD 1.

As already mentioned, a large group of thermoresponsive compounds and polymers are based on PNIPAM. There is accordingly also a wide variety of PNIPAM derivatives, copolymers (simple copolymers, triblock copolymers, et cetera) for producing TRPs having a wide choice of phase transition temperatures, rheological properties, and even sensitivity to other parameters that change such as pH and/or salt concentration.

In a first embodiment, a PNIPAM copolymer is chosen in order to describe a possible way of producing a heat-sensitive OVD 1. The copolymer is comprised mostly of N-isopropyl acid and a small proportion (<1%) of an acrylic acid that contains the necessary reactive group RG for attachment to hyaluronic acid. The proportion of acrylic acid should generally be as small as possible so as not to adversely affect the thermosensitive properties of PNIPAM and to avoid possible attachment to more than one reactive group.

In another embodiment, further modifications to adjust the phase transition temperature are made, since pure PNIPAM has a phase transition temperature of about 32° C. This is achieved for example by copolymerization with other acrylates and/or by adjusting the polymer chain length. For this purpose, the availability of many different acrylic acid derivatives is advantageous, the acrylic chain reaction polymerization allowing the combination of a variety of different acrylic acid derivatives into polyacrylates having varying properties.

However, it must be pointed out that the present invention is not limited to PNIPAM and derivatives thereof. Any suitable polymer that exhibits an appropriate phase transition at a desired threshold temperature can essentially be used for the purposes of the present invention. Examples include thermoresponsive compounds 3 that meet the following requirements:

They have a reactive group for attachment to the OVDP or can be modified (for example by cross-polymerization) with such a reactive group.

They are biocompatible in a way that does not harm the patient's intraocular environment during or after cataract surgery.

If microparticles are to be used, the thermoresponsive compound must be suitable for the production of such particles.

Choice of Attachment Mechanism

As with the selection of TRPs, there are numerous chemical reaction types that can be used to link TRPs to OVDPs. A number of reaction types are listed below, although this list is not exhaustive.

One embodiment includes modifying a PNIPAM copolymer with a primary amine function and attaching it directly to the carboxyl function of the HA by means of an EDC/NHS coupling.

Figure 6:
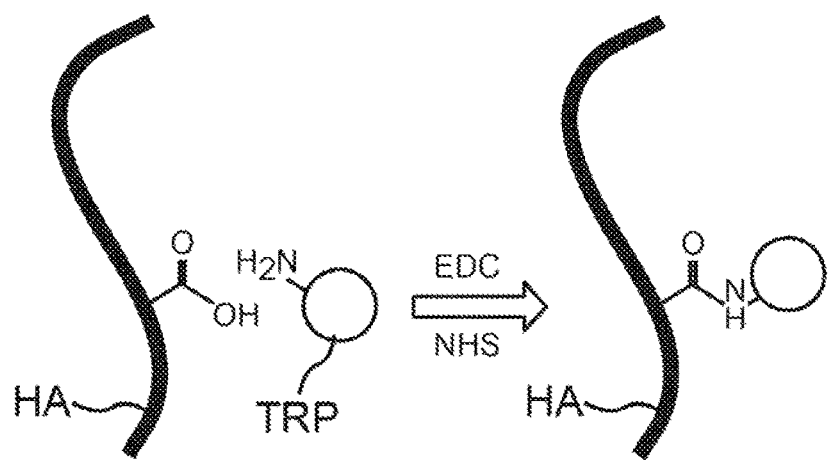
FIG. 6 shows a mechanism for direct attachment of a thermoresponsive compound to hyaluronic acid by means of EDC/NHS-mediated peptide coupling.

This mechanism for the direct attachment of a TRP to hyaluronic acid (or other suitable polymer) by means of an EDC/NHS-mediated peptide coupling is shown in FIG. 6. In some instances, the TRP is first modified with a primary amine, either by copolymerizing an appropriately modified acrylic acid bearing such a primary amine or by functionalizing the polymer using another reaction. In this connection, it is pointed out that the term "acrylic acid" or "acrylate" in the context of the present disclosure encompasses also alkyl acrylic acids or alkyl acrylates, for example methacrylic acid or methacrylate, ethylacrylic acid, ethyl acrylate, et cetera.

Figure 7:
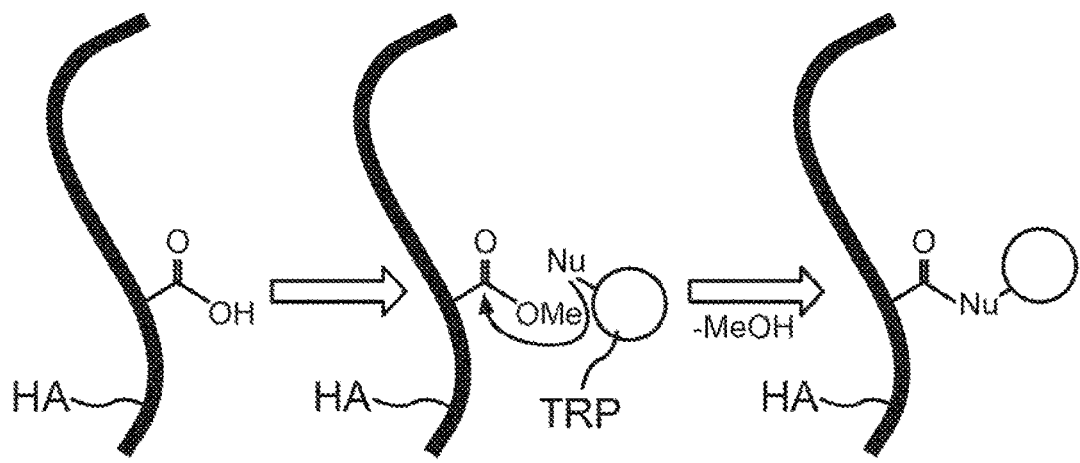
FIG. 7 shows a mechanism for direct attachment of a thermoresponsive compound to hyaluronic acid by nucleophilic substitution.

Alternatively, in some instances, the carboxyl groups of HA (or other suitable polymer) are converted into ester groups, which subsequently react with a nucleophilic group of the PNIPAM copolymer (or other TRP) through a nucleophilic substitution. Such a mechanism of direct attachment of a TRP to hyaluronic acid through nucleophilic substitution is shown in FIG. 7 by way of example. For this purpose, the carboxyl group of the HA is first methoxylated, which permits subsequent attack by a nucleophilic group of the TRP. This additional reaction step allows the TRP to be selected more flexibly, since, compared to FIG. 6, a larger selection of reactive groups can be considered as co-reactants.

In other embodiments, "click chemistry" is used to combine the two starting materials with one another, for example Michael addition or Diels-Alder addition. Since both the hyaluronic acid (or other viscoelastic polymers) and the PNIPAM copolymers (or other thermoresponsive compounds) are easily modifiable, it is possible to introduce a variety of reactive groups and access a large number of possible linking reactions.

In some embodiments, to increase the distance between the viscoelastic polymer and the thermoresponsive compound, the same chemical reaction types are used for the coupling of spacers. This is accomplished either through use as a crosslinker or through attachment to the HA or TRP before the reaction. An example of a spacer is functionalized polyethylene glycol (PEG), which has been well explored with a variety of possible functional groups. Furthermore, it is generally known that PEG has a very favorable toxicity profile.

Figure 8:
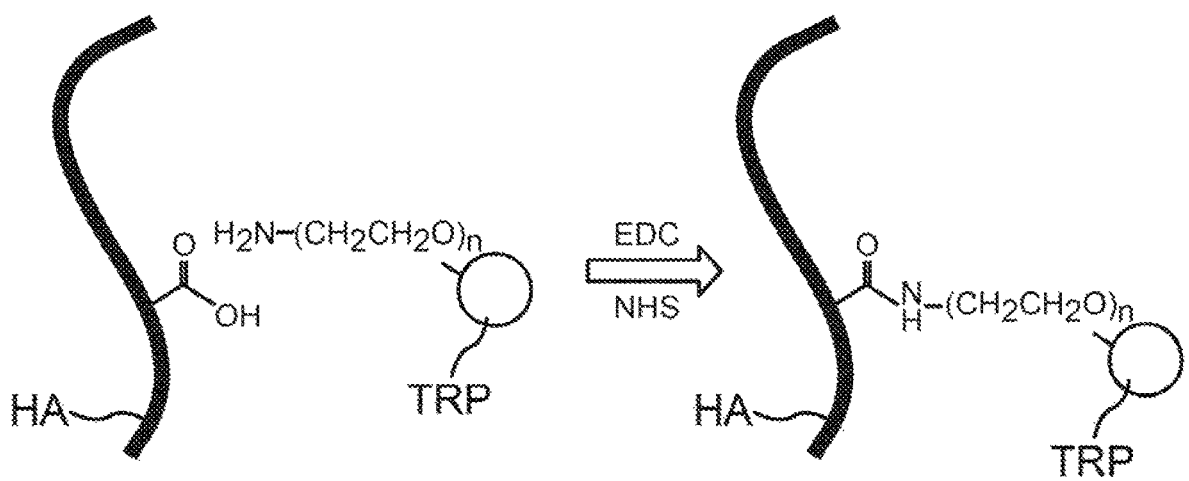
FIG. 8 shows a mechanism for implementing spacers between the thermoresponsive compound and hyaluronic acid; and, FIG. 9 shows a basic illustration of a detection apparatus for eye surgery.

FIG. 8 shows a method for implementing spacers between the TRP and the hyaluronic acid to increase the distance apart. The TRP is modified with a spacer that bears a terminal primary amine that is then in some embodiments coupled to the carboxyl group of the hyaluronic acid in the manner already described. This is achieved by producing a PEG having an acrylic acid function at one end and a primary amine at the other end of the polymer chain and then copolymerizing this with the TRP.

Here too, it should be noted that, while the EDC/NHS-mediated peptide coupling is used in the examples for attaching a TRP to hyaluronic acid, it is just one of many possible methods by which this can be achieved. In the field of chemistry there is a large number of other possible mechanisms.

The additional property of thermoresponsiveness is generally applicable to all OVD types. It offers great potential for reducing the risk of thermal injury to eye structures. Particular great advantages result in the case of dispersive OVDs, which are typically used during surgery to protect the corneal endothelium, which does not regenerate. Intraoperative surgical trauma can cause irreversible endothelial damage. Since wound healing or regeneration of the corneal endothelium do not occur, a dispersive OVD 1 having thermoresponsive properties offers both coating protection of the corneal endothelium and also a temperature sensor on the corneal endothelium. They thus provide important information about temperature changes in this sensitive cell layer.

With the aid of the present disclosure, automatic detection of the OVD coloration/turbidity via an imaging sensor integrated for example in the surgical microscope can moreover permit the output of a warning signal by a human-machine interface 8 (FIG. 9) when the registered temperature exceeds a critical threshold temperature. Furthermore, automatic adjustment of the parameters of a phaco machine is possible when there is an appropriate cabled and/or wireless interface between the optical sensor system 6/human-machine interface 8 and the phaco machine.

Figure 9:
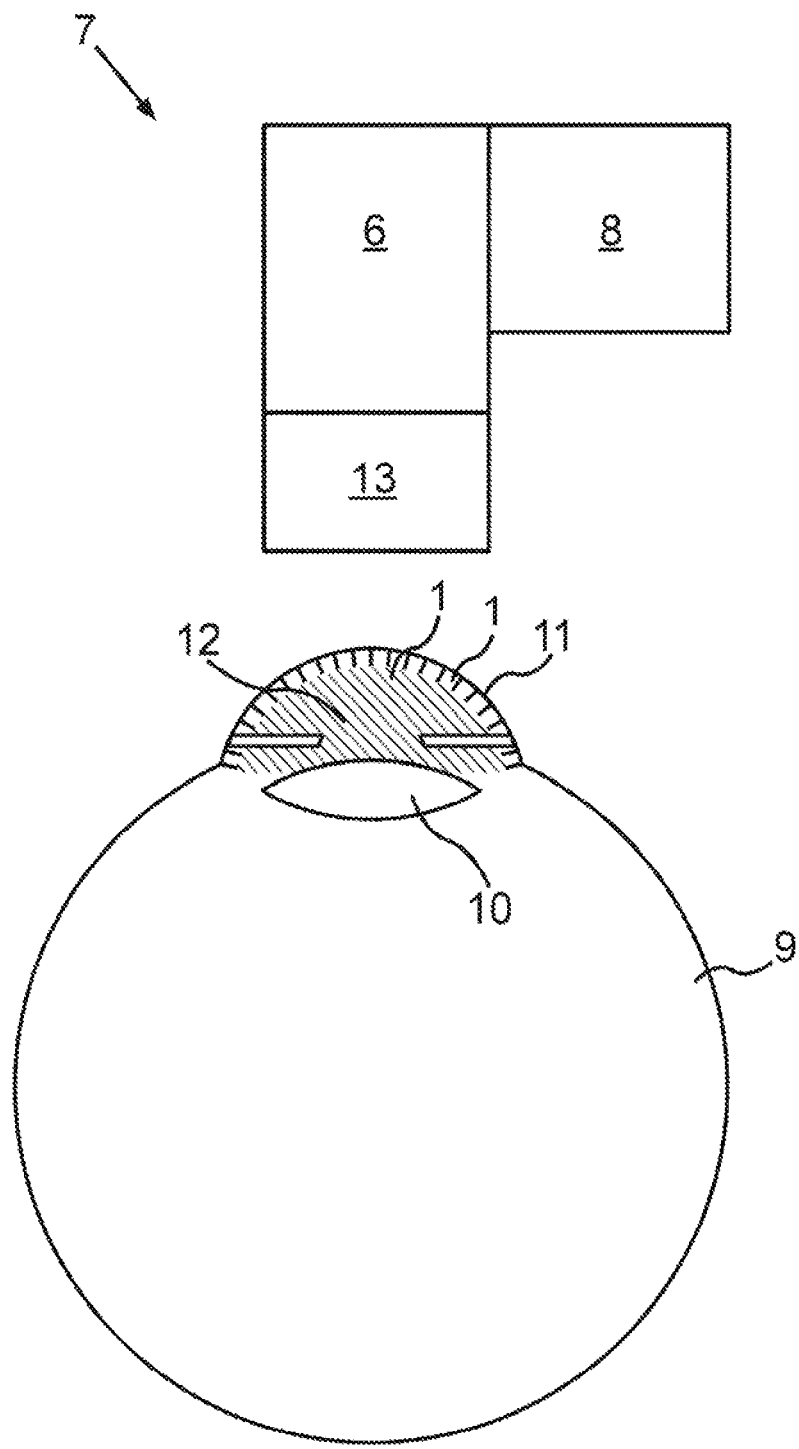

FIG. 9 shows for this purpose a basic illustration of a detection apparatus 7 for surgery on a human eye or animal eye 9, the surgery being by way of example a phacoemulsification of a lens 10 for the treatment of a cataract. The detection apparatus 7 comprises at least one optical sensor system 6, by means of which a discontinuous change in a physical property from the group color and transmittance of a thermoresponsive OVD 1 of the invention can be detected. In the working example shown, the sensor system 6 is integrated into a surgical microscope, but it can in principle also be present as a separate system or be integrated in another system. In addition, the detection apparatus 7 in some embodiments comprises at least one human-machine interface 8 coupled to the sensor system 6 for the purposes of data exchange, by means of which a visual and/or acoustic and/or haptic indication to a user can be generated in the event of detection of a discontinuous change in the optical properties of the OVD 1. If necessary, the detection apparatus 7 can have an essentially optional optical filter 13 in order to improve the detection of the OVD 1.

It can be seen that the described thermoresponsive OVD 1 allows application not only on the anterior surface of the cornea (when it is applied to the cornea 11 from the outside, for example), but also on the intraocular structures (when it is introduced into the anterior chamber 12, for example). The OVD 1 is in such embodiments delivered in syringes equipped with a Luer lock safety system. However, other forms of delivery and application are of course also conceivable.

The parameter values specified in the documents to define process and measurement conditions for the characterization of specific properties of the subject matter described herein should also be considered to be encompassed by the scope of the invention in the context of deviations—for example due to measurement errors, system errors, DIN tolerances, and the like.

It is understood that the foregoing description is that of the preferred embodiments of the invention and that various changes and modifications may be made thereto without departing from the spirit and scope of the invention as defined in the appended claims.

LIST OF REFERENCE SIGNS

1 Ophthalmological composition (OVD)
2 Viscoelastic polymer (OVDP)
3 Thermoresponsive compound (TRP)
4 Sample vessel
5 Coordinate system
6 Sensor system
7 Detection apparatus
8 Human-machine interface
9 Eye
10 Lens
11 Cornea
12 Anterior chamber
13 Filter
HA Hyaluronic acid
RG Reactive group
CL Crosslinker
$T_T$ Temperature threshold
Nu Nucleophile

What is claimed is:

1. An ophthalmological composition comprising at least one viscoelastic polymer,
wherein said composition comprises at least one thermoresponsive compound that in a predefined wavelength range undergoes a temperature-dependent discontinuous change in at least one physical property from a group color and transmittance.

2. The ophthalmological composition as claimed in claim 1,
wherein
a temperature-dependent change in the at least one physical property is reversible and/or wherein the temperature-dependent change in the at least one physical property occurs within not more than 10 seconds after a predefined temperature threshold value has been exceeded.

3. The ophthalmological composition as claimed in claim 1,
wherein the at least one thermoresponsive compound is selected from one or more of polymers, interpenetrating polymer networks, semi-interpenetrating polymer networks, liquid crystals, pigments, dyes, inks, and microcapsules.

4. The ophthalmological composition as claimed in claim 3,
wherein the at least one thermoresponsive compound comprises at least one constitutional unit selected from poly(N-isopropylacrylamide), poly(N,N-diethylacrylamide), poly(methyl vinyl ether), poly(N-vinylcaprolactam), a block copolymer of poly(ethylene oxide) and poly(propylene oxide), a poly(pentapeptide) of elastin, an interpenetrating network of polyacrylamide and polyacrylic acid, and/or copolymers thereof.

5. The ophthalmological composition as claimed in claim 1,
wherein the at least one viscoelastic polymer comprises a polysaccharide selected from glycosaminoglycans, cellulose, a cellulose ether with methyl and/or ethyl and/or propyl groups, and pharmacologically acceptable salts thereof.

6. The ophthalmological composition as claimed in claim 1,
wherein the at least one thermoresponsive compound is covalently linked to the at least one viscoelastic polymer,
wherein the at least one thermoresponsive compound is present in the form of particles and/or microspheres dispersed in the at least one viscoelastic polymer, and/or
wherein the at least one viscoelastic polymer and the at least one thermoresponsive compound form a semi-interpenetrating and/or interpenetrating network.

7. The ophthalmological composition as claimed in claim 1,
wherein the at least one thermoresponsive compound exhibits thermochromic and/or thermotropic behavior when a predefined temperature value ($T_s$) within a temperature range of between 10° C. and 80° C. is exceeded, and/or
wherein the at least one thermoresponsive compound has, in a first temperature range below 60° C., a first color and/or transmission property and, in a second temperature range that is above the first temperature range, a second color and/or transmission property that is different from the first color and/or transmission property.

8. The ophthalmological composition as claimed in claim 7,
wherein the at least one thermoresponsive compound is in the first temperature range essentially colorless and/or essentially transparent, and/or
wherein the at least one thermoresponsive compound is in the second temperature range colored and/or essentially non-transparent.

9. The ophthalmological composition as claimed in claim 1,
wherein the predefined wavelength range is between 50 μm and 200 nm.

10. The ophthalmological composition as claimed in claim 1, wherein the at least one viscoelastic polymer comprises a polysaccharide selected from hydroxypropylmethylcellulose, hydroxyethylmethylcellulose and/or methylcellulose, a glycosaminoglycan, and/or any mixture thereof, or copolymers thereof.

11. The ophthalmological composition as claimed in claim 10, wherein the at least one viscoelastic polymer comprises hyaluronic acid, chondroitin sulfate, dermatan sulfate, heparin, heparan sulfate, keratan sulfate, alginic acid, polymannuronic acid, polyguluronic acid, polyglucuronic acid, amylose, amylopectin, callose, chitosan, polygalactomannan, dextran, xanthan, and/or any mixture thereof, or copolymers thereof.

12. The ophthalmological composition as claimed in claim 6, wherein the at least one thermoresponsive compound is covalently linked to the at least one viscoelastic polymer via a spacer.

13. The ophthalmological composition as claimed in claim 7, wherein the at least one thermoresponsive compound has, in a first temperature range below 40° C., a first color and/or transmission property and, in a second temperature range that is above the first temperature range, a second color and/or transmission property that is different from the first color and/or transmission property.

14. The ophthalmological composition as claimed in claim 7, wherein the at least one thermoresponsive compound has, in a first temperature range below 35° C., a first color and/or transmission property and, in a second temperature range that is above the first temperature range, a second color and/or transmission property that is different from the first color and/or transmission property.

15. The ophthalmological composition as claimed in claim 1, wherein the predefined wavelength range is between 780 nm and 315 nm.

\* \* \* \* \*

UNITED STATES PATENT AND TRADEMARK OFFICE
CERTIFICATE OF CORRECTION

PATENT NO. : 12,390,561 B2
APPLICATION NO. : 17/891837
DATED : August 19, 2025
INVENTOR(S) : Masch et al.

It is certified that error appears in the above-identified patent and that said Letters Patent is hereby corrected as shown below:

In the Specification

In Column 11: Line 55, delete:

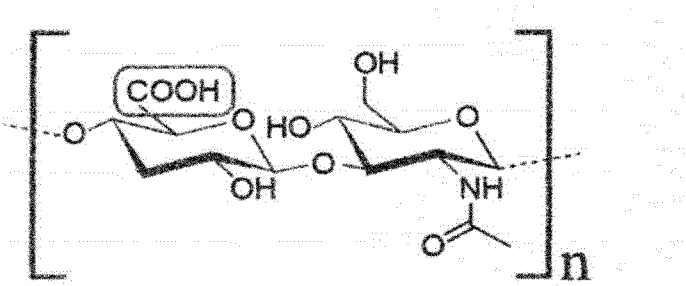

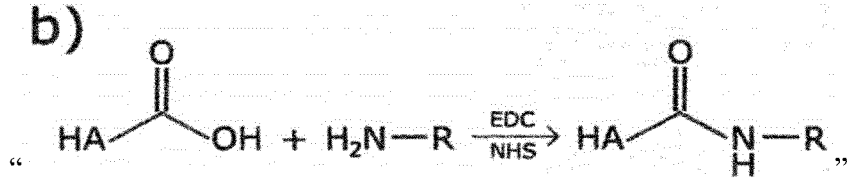

And substitute:

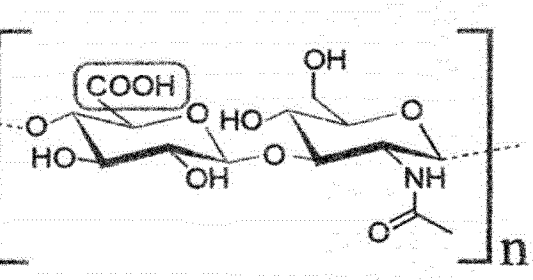

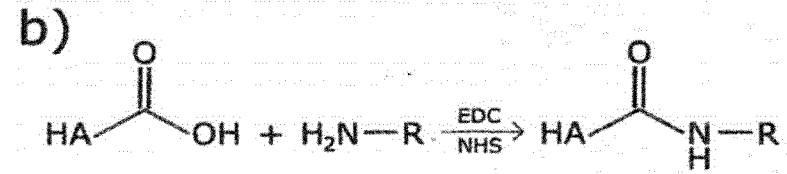

Signed and Sealed this
Twenty-third Day of December, 2025

John A. Squires
*Director of the United States Patent and Trademark Office*